(12) United States Patent
Keshamouni et al.

(10) Patent No.: US 11,226,333 B2
(45) Date of Patent: Jan. 18, 2022

(54) LUNG CANCER SIGNATURE

(71) Applicant: The Regents of the University of Michigan, Ann Arbor, MI (US)

(72) Inventors: Venkateshwar G. Keshamouni, Canton, MI (US); Gilbert S. Omenn, Ann Arbor, MI (US); Guoan Chen, Ann Arbor, MI (US); David G. Beer, Chelsea, MI (US); Theodore J. Standiford, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/169,048

(22) Filed: Oct. 24, 2018

(65) Prior Publication Data

US 2019/0056403 A1 Feb. 21, 2019

Related U.S. Application Data

(62) Division of application No. 14/540,614, filed on Nov. 13, 2014, now abandoned.

(60) Provisional application No. 61/904,711, filed on Nov. 15, 2013.

(51) Int. Cl.
*C12Q 1/6886* (2018.01)
*G01N 33/574* (2006.01)

(52) U.S. Cl.
CPC ..... *G01N 33/57423* (2013.01); *C12Q 1/6886* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 6,248,526 | B1 * | 6/2001 | Weimer | C12Q 1/6846 435/6.11 |
| 6,582,908 | B2 | 6/2003 | Fodor | |
| 2001/0051344 | A1 * | 12/2001 | Shalon | B01L 3/0244 435/6.11 |
| 2011/0294684 | A1 * | 12/2011 | Baty | C12Q 1/6886 506/9 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Lucentini (The Scientist, 2004, vol. 18, p. 20) (Year: 2004).*
Arribalzaga et al., "New tumor, node, metastasis staging system for lung cancer." J Thorac Oncol. Oct. 2009; 4(10):1301.
Azzoli et al., "Can adjuvant chemotherapy improve survival in patients with early-stage, resected non-small-cell lung cancer?" Nat Clin Pract Oncol. Nov. 2005; 2(11):552-3.
Ben-Porath et al., "An embryonic stem cell-like gene expression signature in poorly differentiated aggressive human tumors." Nat Genet. May 2008; 40(5):499-507.
Bild, "Oncogenic pathway signatures in human cancers as a guide to targeted therapies" Nature Jan. 19, 2006, 439:353-357.
Buyse et al., "Validation and clinical utility of a 70-gene prognostic signature for women with node-negative breast cancer." J Natl Cancer Inst. Sep. 6, 2006;98(17):1183-92.
Detterbeck et al., "The new lung cancer staging system." Chest. Jul. 2009; 136(1):260-71.
Domont et al., "Adjuvant chemotherapy in early-stage non-small cell lung cancer." Semin Oncol. Jun. 2005; 32(3):279-83.
Waller et al., "Chemotherapy for patients with non-small cell lung cancer: the surgical setting of the Big Lung Trial." Eur J Cardiothorac Surg. Jul. 2004; 26(1):173-82.
Faivre et al., "New paradigms in anticancer therapy: targeting multiple signaling pathways with kinase inhibitors." Semin Oncol. Aug. 2006; 33(4):407-20.
Felip et al., "ESMO Minimum Clinical Recommendations for diagnosis, treatment and follow-up of non-small-cell lung Dancer (NSCLC)." Ann Oncol. 2005; 16 Suppl 1:i28-9.
Gail et al., "Prognostic factors in patients with resected stage I non-small cell lung cancer. A report from the Lung Cancer Study Group." Cancer. Nov. 1, 1984; 54(9):1802-13.
Garber et al., "Diversity of gene expression in adenocarcinoma of the lung." Proc Natl Acad Sci U S A. Nov. 20, 2001; 98(24):13784-9.
Harpole et al., "A prognostic model of recurrence and death in stage I non-small cell lung cancer utilizing presentation, histopathology, and oncoprotein expression." Cancer Res. Jan. 1, 1995; 55(1):51-6.
Hassan et al., "An embryonic stem cell-like signature identifies poorly differentiated lung adenocarcinoma but not squamous cell carcinoma." Clin Cancer Res. Oct. 15, 2009; 15(20):6386-90.
Horio et al., "Prognostic significance of p53 mutations and 3p deletions in primary resected non-small cell lung cancer." Cancer Res. Jan. 1, 1993; 53(1):1-4.
Ichinose et al., "Is T factor of the TNM staging system a predominant prognostic factor in pathologic stage I non-small-cell lung cancer ? A multivariate prognostic factor analysis of 151 patients." J Thorac Cardiovasc Surg. Jul. 1993; 106(1):90-4.
Johnson & Rabin, "Patient subsets benefiting from adjuvant therapy following surgical resection of non-small cell lung cancer." Clin Cancer Res. Jul. 1, 2005;11(13 Pt 2):5022s-5026s.
Keller et al., "A randomized trial of postoperative adjuvant therapy in patients with completely resected stage II or IIIA non-small-cell lung cancer. Eastern Cooperative Oncology Group." N Engl J Med. Oct. 26, 2000; 343(17):1217-22.
Keshamouni et al., "Differential protein expression profiling by iTRAQ-2DLC-MS/MS of lung cancer cells undergoing epithelial-mesenchymal transition reveals a migratory/invasive phenotype." J Proteome Res. May 2006;5(5):1143-54.

(Continued)

*Primary Examiner* — Katherine D Salmon
(74) *Attorney, Agent, or Firm* — Casimir Jones, S.C.; Tanya A. Arenson

(57) ABSTRACT

The present disclosure relates to compositions and methods for cancer diagnosis, research and therapy, including but not limited to, cancer markers. In particular, the present disclosure relates to cancer markers as diagnostic markers and clinical targets for lung cancer.

4 Claims, 6 Drawing Sheets

(56) References Cited

OTHER PUBLICATIONS

Keshamouni et al., "Temporal quantitative proteomics by iTRAQ 2D-LC-MS/MS and corresponding mRNA expression analysis identify post-transcriptional modulation of actin-cytoskeleton regulators during TGF-beta-Induced epithelial-mesenchymal transition." J Proteome Res. Jan. 2009;8(1):35-47.

Lacroix et al., "Gene expression profiling of non-small-cell lung cancer." Expert Rev Mol Diagn. Mar. 2008; 8(2):167-78.

Mani et al., "The epithelial-mesenchymal transition generates cells with properties of stem cells." Cell. May 16, 2008; 133(4):704-15.

Okayama et al., "Identification of genes upregulated in ALK-positive and EGFR/KRAS/ALK-negative lung adenocarcinomas." Cancer Res. Jan. 1, 2012; 72(1):100-11.

Paik et al., "Development and clinical utility of a 21-gene recurrence score prognostic assay in patients with early breast cancer treated with tamoxifen." Oncologist. Jun. 2007;12(6):631-5.

Ramaswamy et al., "A molecular signature of metastasis in primary solid tumors." Nat Genet. Jan. 2003; 33(1):49-54.

Raponi et al., "Gene expression signatures for predicting prognosis of squamous cell and adenocarcinomas of the lung." Cancer Res. Aug. 1, 2006; 66(15):7466-72.

Reka et al., "Identifying inhibitors of epithelial-mesenchymal transition by connectivity map-based systems approach" J Thorac Oncol. Nov. 2011; 6(11):1784-92.

Reka et al., "Peroxisome proliferator-activated receptor-gamma activation inhibits tumor metastasis by antagonizing Smad3-mediated epithelial-mesenchymal transition." Mol Cancer Ther. Dec. 2010; 9(12):3221-32.

Rodenhuis et al., "Mutational activation of the K-ras oncogene. A possible pathogenetic factor in adenocarcinoma of the lung." N Engl J Med. Oct. 8, 1987; 317(15):929-35.

Scagliotti et al., "Randomized study of adjuvant chemotherapy for completely resected stage I, II, or IIIA non-small-cell Lung cancer." J Natl Cancer Inst. Oct. 1, 2003; 95(19):1453-61.

Shedden et al., "Gene expression-based survival prediction in lung adenocarcinoma: a multi-site, blinded validation study." Nat Med. Aug. 2008; 14(8):822-7.

Slebos et al., "K-ras oncogene activation as a prognostic marker in adenocarcinoma of the lung." N Engl J Med. Aug. 30, 1990; 323(9):561-5.

Sun et al., "New molecularly targeted therapies for lung cancer." J Clin Invest. Oct. 2007; 117(10):2740-50.

Takise et al., "Histopathologic prognostic factors in adenocarcinomas of the peripheral lung less than 2 cm in diameter." Cancer. May 15, 1988; 61(10):2083-8.

Visbal et al., "Adjuvant Chemotherapy for Early-Stage Non-small Cell Lung Cancer." Chest. Oct. 2005; 128(4):2933-43.

NEB catalog (1998/1999 pp. 121, 284).

RHEE (Applied and Environment Microbiology Jul. 2004 p. 4303).

* cited by examiner

LUNG CANCER SIGNATURE

The present application is a divisional of U.S. patent application Ser. No. 14/540,614, filed Nov. 13, 2014, which claims priority to U.S. Provisional Patent Application No. 61/904,711, filed Nov. 15, 2013, the contents of which are herein incorporated by reference in their entireties.

FIELD OF THE INVENTION

The present disclosure relates to compositions and methods for cancer diagnosis, research and therapy, including but not limited to, cancer markers. In particular, the present disclosure relates to cancer markers as diagnostic markers and clinical targets for lung cancer.

BACKGROUND OF THE INVENTION

Lung cancer remains the leading cause of cancer death in industrialized countries. About 75 percent of lung cancer cases are categorized as non-small cell lung cancer (e.g., adenocarcinomas), and the other 25 percent are small cell lung cancer. Lung cancers are characterized in to several stages, based on the spread of the disease. In stage I cancer, the tumor is only in the lung and surrounded by normal tissue. In stage II cancer, cancer has spread to nearby lymph nodes. In stage III, cancer has spread to the chest wall or diaphragm near the lung, or to the lymph nodes in the mediastinum (the area that separates the two lungs), or to the lymph nodes on the other side of the chest or in the neck. This stage is divided into IIIA, which can usually be operated on, and stage IIIB, which usually cannot withstand surgery. In stage IV, the cancer has spread to other parts of the body.

Most patients with non-small cell lung cancer (NSCLC) present with advanced stage disease, and despite recent advances in multi-modality therapy, the overall ten-year survival rate remains dismal at 8-10% (Fry et al., Cancer 86:1867 [1999]). However, a significant minority of patients, approximately 25-30%, with NSCLC have pathological stage I disease and are usually treated with surgery alone. While it is known that 35-50% of patients with stage I disease will relapse within five years (Williams et al., Thorac. Cardiovasc. Surg. 82:70 [1981]; Pairolero et al., Ann, Thorac. Surg. 38:331 [1984]), it is not currently possible to identify which specific patients are at high risk of relapse.

Adenocarcinoma is currently the predominant histologic subtype of NSCLC (Fry et al., supra; Kaisermann et al., Brazil Oncol. Rep. 8:189 [2001]; Roggli et al., Hum. Pathol. 16:569 [1985]). While histopathological assessment of primary lung carcinomas can roughly stratify patients, there is still an urgent need to identify those patients who are at high risk for recurrent or metastatic disease by other means. Previous studies have identified a number of preoperative variables that impact survival of patients with NSCLC (Gail et al., Cancer 54:1802 1984]; Takise et al., Cancer 61:2083 [1988]; Ichinose et al., J. Thorac. Cardiovasc. Surg. 106:90 [1993]; Harpole et al., Cancer Res. 55:1995]). Tumor size, vascular invasion, poor differentiation, high tumor proliferate index, and several genetic alterations, including K-ras (Rodenhuis et al., N. Engl. J. Med. 317:929 [1987]; Slebos et al., N. Engl. J. Med. 323:561 [1990]) and p53 (Harpole et al., supra; Horio et al., Cancer Res. 53:1 [1993]) mutation, have been reported as prognostic indicators.

Tumor stage is an important predictor of patient survival, however, much variability in outcome is not accounted for by stage alone, as is observed for stage I lung adenocarcinoma which has a 65-70% five-year survival (Williams et al., supra; Pairolero et al., supra). Current therapy for patients with stage I disease usually consists of surgical resection and no additional treatment (Williams et al., supra; Pairolero et al., supra). The identification of a high-risk group among patients with stage I disease would lead to consideration of additional therapeutic intervention for this group, as well as leading to improved survival of these patients.

There is a need for additional diagnostic and treatment options, particularly treatments customized to a patient's tumor.

SUMMARY OF THE INVENTION

The present disclosure relates to compositions and methods for cancer diagnosis, research and therapy, including but not limited to, cancer markers. In particular, the present disclosure relates to cancer markers and panels of cancer markers as diagnostic markers and clinical targets for lung cancer. In some embodiments, the present invention provides compositions, kits, systems and methods for determining the likelihood of survival of a subject based on altered expression of one or more cancer markers.

For example, in some embodiments, the present invention provides a kit for characterizing cancer (e.g., determining likelihood of survival, likelihood of metastasis (e.g., lymph node metastasis), or likelihood of advancement) in a subject diagnosed with lung cancer, comprising: reagents for detection of altered expression of one or more (e.g., 2 or more, 3 or more, 4 or more, 5 or more, 10 or more, 15 or more or all of) HMGA2, LAMC2, EIF4EBP1, FN1, HSPB1, ULBP2, VEGFA, BMP1, FST, CD59, TNFRSF12A, PDGFB, COL4A3, SERPINE1, SCG2, TGFB1, HMOX1, STC1, XYLT1, or PPP1R14B. In some embodiments, the kits further comprises reagents for detecting one or more of ADAM19, ANGPTL4, AP1S2, ARPC4, BPGM, CD151, CHST11, CHST3, COL1A1, COL4A1, COL4A2, COL7A1, CRIP2, VCAN, CTGF, CXCL12, CYR61, DSC2, ECM1, EFNA1, EPHB2, FHL2, FSTL1, FSTL3, C11orf41, GALNT2, GSN, IGF1, IGF2, IGFBP5, IGFBP7, IL11, INHBA, ITGA2, ITGA3, JAG1, MGC17330, KIAA1797, LEFTY2, LIF, LTBP1, LTBP2, LTBP3, LTBP4, PIK3IP1, MMP1, MMP10, MMP2, MMP9, MRC2, NPC2, NPTX1, NRG1, PAWR, PCDH1, PDLIM2, PGRMC2, PLAT, PLAUR, PLOD2, PLSCR3, HTRA1, PTPRK, RSU1, SEMA3C, SERPINE2, SPOCK1, TAGLN, TAGLN2, TAX1BP3, TGFBR1, THBS1, TIMP2, TLL2, TNFAIP6, TP53I3, or TUBA4B. In some embodiments, markers are detected in a multiplex or panel format comprising 5 or more, 10 or more, 15 or more, or all of the aforementioned markers.

The present invention also provides a composition comprising one or more reaction mixtures (e.g., at least 5, at least 10, at least 15, or corresponding to all of the genes), each reaction mixture comprising a complex of a reagent for detection of one or more genes selected from, for example, HMGA2, LAMC2, EIF4EBP1, FN1, HSPB1, ULBP2, VEGFA, BMP1, FST, CD59, TNFRSF12A, PDGFB, COL4A3, SERPINE1, SCG2, TGFB1, HMOX1, STC1, XYLT1, PPP1R14B GPTL4, AP1S2, ARPC4, BPGM, CD151, CHST11, CHST3, COL1A1, COL4A1, COL4A2, COL7A1, CRIP2, VCAN, CTGF, CXCL12, CYR61, DSC2, ECM1, EFNA1, EPHB2, FHL2, FSTL1, FSTL3, C11orf41, GALNT2, GSN, IGF1, IGF2, IGFBP5, IGFBP7, IL11, INHBA, ITGA2, ITGA3, JAG1, MGC17330, KIAA1797, LEFTY2, LIF, LTBP1, LTBP2, LTBP3, LTBP4, PIK3IP1, MMP1, MMP10, MMP2, MMP9, MRC2, NPC2, NPTX1, NRG1, PAWR, PCDH1, PDLIM2, PGRMC2, PLAT, PLAUR, PLOD2, PLSCR3, HTRA1, PTPRK, RSU1, SEMA3C, SERPINE2, SPOCK1, TAGLN, TAGLN2, TAX1BP3, TGFBR1, THBS1, TIMP2, TLL2, TNFAIP6, TP53I3, or TUBA4B bound to the gene. In some embodiments, the reagents are, for example, nucleic acid probes that bind to a nucleic acid encoding the gene, a pair of amplification primers that bind to a nucleic acid encoding the gene, a sequencing primer that binds to a nucleic acid encoding the gene, and an antibody that binds to a polypeptide encoded by the gene.

In other embodiments, the present invention provides methods for for characterizing cancer (e.g., determining likelihood of survival, likelihood of metastasis (e.g., lymph node metastasis), or likelihood of advancement) in a subject diagnosed with lung cancer, comprising: contacting a sample from a subject diagnosed with lung with reagents for detection of altered expression of one or more (e.g., 2 or more, 3 or more, 4 or more, 5 or more, 10 or more, 15 or more or all of) HMGA2, LAMC2, EIF4EBP1, FN1, HSPB1, ULBP2, VEGFA, BMP1, FST, CD59, TNFRSF12A, PDGFB, COL4A3, SERPINE1, SCG2, TGFB1, HMOX1, STC1, XYLT1, or PPP1R14B. In some embodiments, the method further comprises detecting one or more of ADAM19, ANGPTL4, AP1S2, ARPC4, BPGM, CD151, CHST11, CHST3, COL1A1, COL4A1, COL4A2, COL7A1, CRIP2, VCAN, CTGF, CXCL12, CYR61, DSC2, ECM1, EFNA1, EPHB2, FHL2, FSTL1, FSTL3, C11orf41, GALNT2, GSN, IGF1, IGF2, IGFBP5, IGFBP7, IL11, INHBA, ITGA2, ITGA3, JAG1, MGC17330, KIAA1797, LEFTY2, LIF, LTBP1, LTBP2, LTBP3, LTBP4, PIK3IP1, MMP1, MMP10, MMP2, MMP9, MRC2, NPC2, NPTX1, NRG1, PAWR, PCDH1, PDLIM2, PGRMC2, PLAT, PLAUR, PLOD2, PLSCR3, HTRA1, PTPRK, RSU1, SEMA3C, SERPINE2, SPOCK1, TAGLN, TAGLN2, TAX1BP3, TGFBR1, THBS1, TIMP2, TLL2, TNFAIP6, TP53I3, or TUBA4B. In some embodiments, the lung cancer is lung adenocarcinoma or squamous cell carcinoma. In some embodiments, the lung cancer is early stage lung cancer or advanced lung cancer.

In some embodiments, the present invention provides a method of a) characterizing cancer in a subject using any of the aforementioned kits and methods; and b) determining a treatment course of action based on said characterizing (e.g., choice of chemotherapeutic agent, surgery, or radiation treatment); and optionally c) administering said treatment. In some embodiments, the method further comprises the step of repeating said characterizing step after said treatment step. In some embodiments, the results of the characterizing are used to alter, stop, start, or modify the treatment course of action.

Further embodiments provide the use of any of the aforementioned compositions and kits in characterizing cancer in a subject diagnosed with lung cancer.

Additional embodiments of the present disclosure are provided in the description and examples below.

DEFINITIONS

Figure 1A:
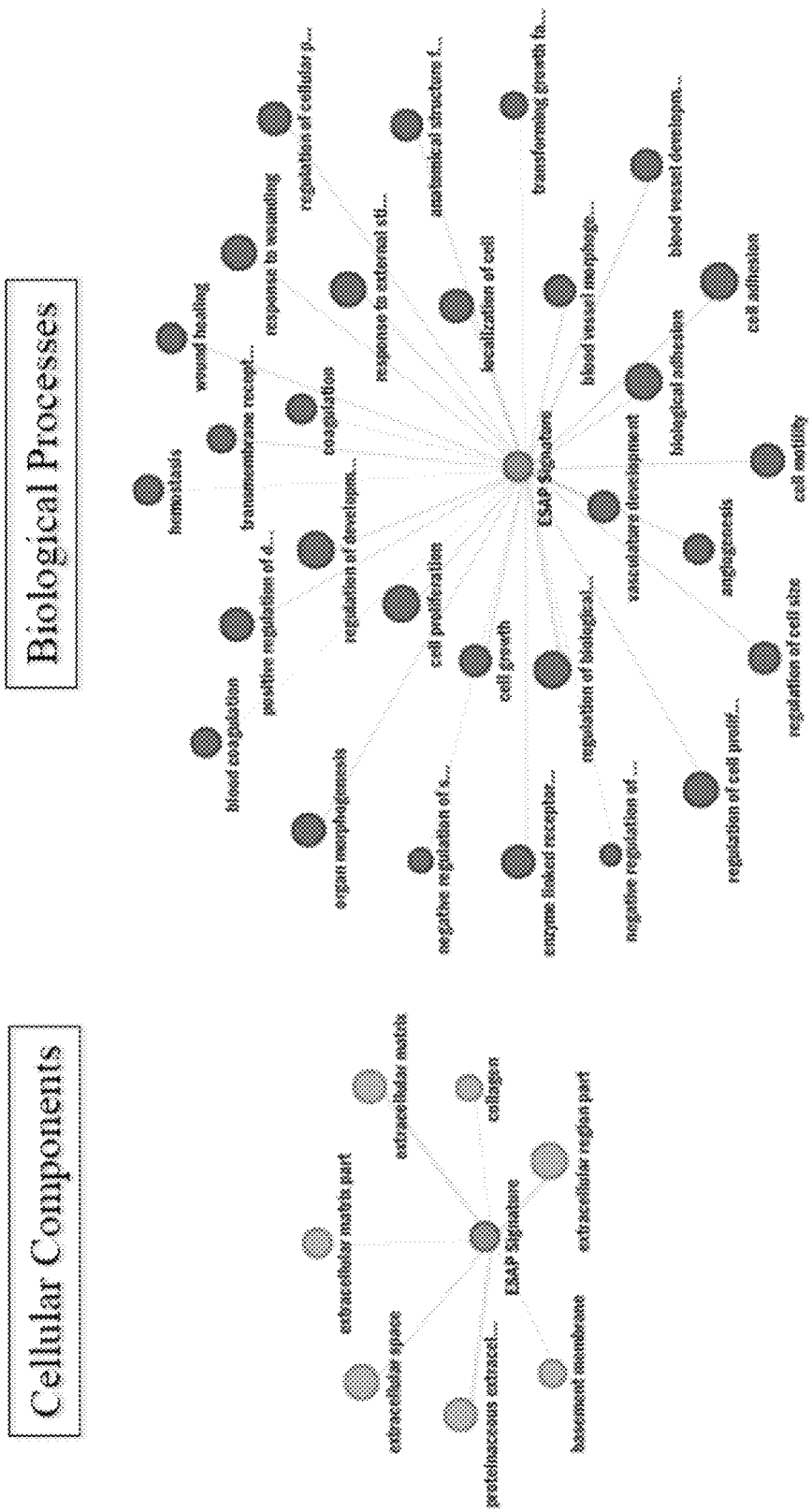
FIG. 1A-B: shows (A) analysis of EMT secretome for enriched biological processes and cellular components and biological processes. (B) cluster analysis of EASP signature and other cancer related pathways in 442 lung adenocarcinomas.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

As used herein, the term "gene upregulated in cancer" refers to a gene that is expressed (e.g., mRNA or protein expression) at a higher level in cancer (e.g., lung cancer) relative to the level in other tissue. In this context, "other tissue" may refer to, for example, tissues from different organs in the same subject or to normal tissues of the same or different type. In some embodiments, genes upregulated in cancer are expressed at a level between at least 10% to 300% higher than the level of expression in other tissue. For example, genes upregulated in cancer are frequently expressed at a level preferably at least 25%, at least 50%, at least 100%, at least 200%, or at least 300% higher than the level of expression in other tissue.

As used herein, the term "gene upregulated in lung tissue" or "gene downregulated in lung cancer" refers to a gene that is expressed (e.g., mRNA or protein expression) at a higher or lower level in tissue obtained from lung (e.g., lung cancer tissue or cell) relative to the level in other tissue (e.g., non-cancerous lung tissue or non-lung tissue). In some embodiments, genes upregulated in lung tissue are expressed at a level between at least 10% to 300%. For example, genes upregulated in cancer are frequently expressed at a level preferably at least 25%, at least 50%, at least 100%, at least 200%, or at least 300% higher than the level of expression in other tissues. In some embodiments, genes upregulated in lung tissue are exclusively expressed in lung tissue.

As used herein, the terms "detect", "detecting" or "detection" may describe either the general act of discovering or discerning or the specific observation of a detectably labeled composition.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "probe" refers to an oligonucleotide, whether occurring naturally as in a purified restriction digest or produced synthetically, recombinantly or by PCR amplification, which is capable of hybridizing to at least a portion of another oligonucleotide of interest. A probe may be single-stranded or double-stranded. Probes are useful in the detection, identification and isolation of particular gene sequences. It is contemplated that any probe used in methods of the present disclosure will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the methods or reagents of the present disclosure be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. An isolated nucleic acid is present in a form or setting that is different from that in which it is found in nature. In contrast, non-isolated nucleic acids are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the nucleic acid, oligonucleotide or polynucleotide often will contain, at a minimum, the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., lung tissue biopsy, lavage fluid, exhaled air, etc.), and gases. Biological samples include blood products, such as plasma, serum and the like. Such examples are not however to be construed as limiting the sample types applicable to the present invention.

DETAILED DESCRIPTION OF THE INVENTION

The present disclosure relates to compositions and methods for cancer diagnosis, research and therapy, including but not limited to, cancer markers. In particular, the present disclosure relates to cancer markers as diagnostic markers and clinical targets for lung cancer.

Lung cancer is the leading cause of cancer related death around the world. The advances made in last decade in diagnosis and treatment did not translate into significant overall 5-year survival rates. The tumor-node-metastasis (TNM) staging system combined with pathologic diagnosis has remained the major tool for medical decision making and predicting patient survival (Detterbeck et al., Chest, 2009. 136(1): p. 260-71; Arribalzaga et al., J Thorac Oncol, 2009. 4(10): p. 1301; author reply 1301-2.). However, accumulating evidence indicates that though patients with identical histology, differentiation, location and stage at diagnosis are treated by similar therapy, the survival is most heterogeneous indicating the current methods of tumor classification and staging are not enough for selecting best treatment choice and prognosis. 30-55% of early stage patients who are treated primarily by surgery will have recurrence within 3 years. Recent randomized clinical trails revealed a significant survival advantage in patients receiving chemotherapy after complete resection in the stage IB-IIIA categories (Visbal et al., Chest, 2005. 128(4): p. 2933-43; Waller et al., Eur J Cardiothorac Surg, 2004. 26(1): p. 173-82; Domont et al., Semin Oncol, 2005. 32(3): p. 279-83; Azzoli, Nat Clin Pract Oncol, 2005. 2(11): p. 552-3). This trend indicates a need to explore alternative indicators to understand the underlying prognosis of a given patient, identify the early stage patients at the greater risk of relapse and decide on appropriate treatment strategy that would optimize patient survival.

Experiments conducted during the course of development of embodiments of the present disclosure developed a prognostic gene signature based on the cellular process of epithelial-mesenchymal transition (EMT), which plays a critical role in tumor progression. EMT is considered as an initiating event for distant dissemination of tumor cells and confers many clinically relevant properties to cancer cells, including migratory and invasive capacity, resistance to apoptosis, drug resistance, evasion of host immune surveillance, and tumor stem cell traits. Cells undergoing EMT represent tumor cells with metastatic potential. Therefore, characterizing the secretome of cells in EMT identifies biomarkers that allow monitoring of EMT in tumor progression and provide a prognostic signature to predict recurrance and survival, particularly in early stage patients.

Utilizing a TGF-β-induced EMT model, differentially secreted proteins were profiled by GeLC-MS/MS and spectral counting, in the conditioned media of A549 lung adenocarcinoma cell line cultured in the presence and absence of TGF-β. By integrating the EMT secretome and the EMT gene expression data from iour earlier study (GSE17708) (Slodkowska), a 97 gene EMT Associated Secretory Phenotype (EASP) signature that showed strong correlation to differentiation and stage and predicted survival of lung adenocarcinoma patients in training and independent test sets was idenfited. This set was further refined to a 20 gene signature (rEASP), which performed equally well in predicting survival in exclusivley early stage (Stage I & II) adenocarcinomas as well as squamous cell carcinomas of lung. Meta-analysis on different lung cancer gene expression data sets clearly established the effectiveness of the 20 gene signature in stratifying the lung cancer patients into low, medium and high risk groups with distinct survival times.

Accordingly, in some embodiments, the present invention provides cancer markers and panels of cancer markers for the research, screening and clinical (e.g., prediction of patient survival with early stage lung cancer) applications.

I. Cancer Markers

In some embodiments, the present invention provides cancer markers whose altered expression (e.g., relative to the level of expression in a non-cancerous lung sample) is indicative of cancer (e.g., lung cancer). For example, in some embodiments, the cancer marker comprises one or more (e.g., 2 or more, 3 or more, 4 or more, 5 or more, 10 or more, 15 or more, or all of) HMGA2, LAMC2, EIF4EBP1, FN1, HSPB1, ULBP2, VEGFA, BMP1, FST, CD59, TNFRSF12A, PDGFB, COL4A3, SERPINE1, SCG2, TGFB1, HMOX1, STC1, XYLT1, or PPP1R14B. In some embodiments, one or more additional markers selected from ADAM19, ANGPTL4, AP1S2, ARPC4, BPGM, CD151, CHST11, CHST3, COL1A1, COL4A1, COL4A2, COL7A1, CRIP2, VCAN, CTGF, CXCL12, CYR61, DSC2, ECM1, EFNA1, EPHB2, FHL2, FSTL1, FSTL3, C11orf41, GALNT2, GSN, IGF1, IGF2, IGFBP5, IGFBP7, IL11, INHBA, ITGA2, ITGA3, JAG1, MGC17330, KIAA1797, LEFTY2, LIF, LTBP1, LTBP2, LTBP3, LTBP4, PIK3IP1, MMP1, MMP10, MMP2, MMP9, MRC2, NPC2, NPTX1, NRG1, PAWR, PCDH1, PDLIM2, PGRMC2, PLAT, PLAUR, PLOD2, PLSCR3, HTRA1, PTPRK, RSU1, SEMA3C, SERPINE2, SPOCK1, TAGLN, TAGLN2, TAX1BP3, TGFBR1, THBS1, TIMP2, TLL2, TNFAIP6, TP5313, or TUBA4B are detected. Sequences of the genes can be found, for example, in the GenBank database (NCBI). In some embodiments, expression of the marker is increased or decreased relative to the level in a non-cancerous lung sample (e.g., 5%, 10%, 25%, 50%, 75%, 100% or more altered expression).

In some embodiments, genes for inclusion in the panel are selected based on their ability to characterize cancer (e.g., based on over or under expression of the marker). In some embodiments, statistical techniques (e.g., those described in the experimental section below) are utilized to select the predictive value of genes or panels of genes. In some embodiments, panels are selected for their collective predictive value using any number of statistical techniques (e.g., those described herein).

In some embodiments, markers are detected in a multiplex or panel format comprising 5 or more, 10 or more, 25 or more, 50 or more or all of the aforementioned markers.

II. Antibodies

The cancer marker proteins of the present disclosure, including fragments, derivatives and analogs thereof, may be used as immunogens to produce antibodies having use in the diagnostic, screening, research, and therapeutic methods described herein. The antibodies may be polyclonal or monoclonal, chimeric, humanized, single chain, Fv or Fab fragments. Various procedures can be used for the production and labeling of such antibodies and fragments. See+, e.g., Burns, ed., *Immunochemical Protocols*, 3$^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975).

III. Diagnostic and Screening Applications

Expression levels of the cancer may be detectable as DNA, RNA or protein. The present disclosure provides RNA and protein based diagnostic and screening methods that detect the expression levels of the cancer markers described herein. The present disclosure also provides compositions and kits for diagnostic and screening purposes.

A. Sample

Any sample suspected of containing the cancer markers may be tested according to the methods of the present disclosure. By way of non-limiting example, the sample may be tissue (e.g., a lung biopsy sample), lung related samples (e.g., lavage fluid, exhaled air, sputum, etc.) blood, cell secretions or a fraction thereof (e.g., plasma, serum, exosomes, etc.).

The patient sample typically involves preliminary processing designed to isolate or enrich the sample for the cancer marker(s) or cells that contain the cancer marker(s). A variety of techniques can be used for this purpose, including but not limited to: centrifugation; immunocapture; cell lysis; and, nucleic acid target capture.

B. Detection of RNA

In some preferred embodiments, detection of lung cancer markers (e.g., including but not limited to, those disclosed herein) is detected by measuring the expression of corresponding mRNA in a tissue sample (e.g., lung tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe. An exemplary method for Northern blot analysis is provided in Example 3.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays are utilized for measuring cancer marker mRNA levels. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, the cancer markers are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995, each of which is herein incorporated by reference in its entirety).

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through fluorometric detection means.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. See, e.g., U.S. Pat. No. 5,814,447 (herein incorporated by reference in its entirety).

In some embodiments, nucleic acid sequencing methods are utilized for detection. In some embodiments, the sequencing is Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequencing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, sequencing is nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, sequencing is HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

In some embodiments, sequencing is the technique developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

C. Detection of Protein

In other embodiments, gene expression of cancer markers is detected by measuring the expression of the corresponding protein or polypeptide. Protein expression may be detected by any suitable method. In some embodiments, proteins are detected by immunohistochemistry. In other embodiments, proteins are detected by their binding to an antibody raised against the protein. The generation of antibodies is described above.

Illustrative non-limiting examples of immunoassays include, but are not limited to: immunoprecipitation; Western blot; ELISA; immunohistochemistry; immunocytochemistry; immunochromatography; flow cytometry; and, immuno-PCR. Polyclonal or monoclonal antibodies detectably labeled using various techniques (e.g., colorimetric, fluorescent, chemiluminescent or radioactive labels) are suitable for use in the immunoassays.

Immunoprecipitation is the technique of precipitating an antigen out of solution using an antibody specific to that antigen. The process can be used to identify proteins or protein complexes present in cell extracts by targeting a specific protein or a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and optionally sorting microscopic particles or cells suspended in a stream of fluid. It allows simultaneous multi-parametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In other embodiments, the immunoassay described in U.S. Pat. Nos. 5,599,677 and 5,672,480; each of which is herein incorporated by reference.

D. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or other sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a sputum sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of long term survival) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. Kits

In yet other embodiments, the present invention provides kits, compositions, and systems for the detection and characterization of lung cancer (e.g., by detecting the presence, absence, or level of expression of one or more of the cancer markers described herein). In some embodiments, the kits contain antibodies specific for one or more cancer markers, in addition to detection reagents and buffers. In other embodiments, the kits contain reagents specific for the detection of mRNA, cDNA or protein (e.g., oligonucleotide probes, primers, antibodies, optionally in an array format). In some embodiments, the kits comprise a plurality of probes, primer pairs, or sequencing primers for multiplex detection of one or more (e.g., all) of the cancer markers described herein. For example, in some embodiments, kits or systems comprise a plurality of distinct probes, primer pairs, or sequencing primers, each of which detects a different cancer marker described herein. In preferred embodiments, the kits contain all of the components necessary, sufficient or useful to perform a detection assay, including all controls, directions for performing assays, and any necessary software for analysis and presentation of results.

In some embodiments, kits and systems comprise computer systems (e.g., comprising computer processors, display screens, portable electronics, and the like) for collecting and analyzing data, as well as providing and displaying information to user (e.g., characterization of lung cancer). Systems and methods for analyzing data are described above.

In some embodiments, the present disclosure provides samples comprising a plurality of reaction mixtures each comprising one or more nucleic acids encoding a cancer marker described herein or a cancer marker polypeptide bound to a detection reagent (e.g., probe, primer pair, sequencing primer, antibody, etc.). In some embodiments, each reaction mixture is a reaction mixture for detection of a distance cancer marker nucleic acid or polypeptide.

IV. Drug Screening Applications

In some embodiments, the present disclosure provides drug screening assays (e.g., to screen for anticancer drugs). The screening methods of the present disclosure utilize cancer markers described herein alone or in combination with other markers. For example, in some embodiments, the present disclosure provides methods of screening for compounds that alter (e.g., increase or decrease) the expression of cancer markers. The compounds or agents may interfere with transcription, by interacting, for example, with the promoter region. The compounds or agents may interfere with mRNA. The compounds or agents may interfere with pathways that are upstream or downstream of the biological activity of the cancer marker. In some embodiments, candidate compounds are antisense or interfering RNA agents (e.g., oligonucleotides) directed against cancer markers or other pathway components. In other embodiments, candidate compounds are antibodies or small molecules that specifically bind to a cancer marker regulator or expression products of the present disclosure and inhibit its biological function.

In one screening method, candidate compounds are evaluated for their ability to alter cancer marker expression by contacting a compound with a cell or subject expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method.

In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

EXPERIMENTAL

The following examples are provided in order to demonstrate and further illustrate certain preferred embodiments and aspects of the present disclosure and are not to be construed as limiting the scope thereof.

Example 1

Methods

Cell culture: The A549 human lung adenocarcinoma cell line was obtained from the American type Culture Collection (Manassas, Va.) and maintained in RPMI-1640 medium with glutamine, supplemented with 10% FBS, penicillin, and streptomycin and tested for *mycoplasma* contamination. All tissue culture media and media supplements were purchased from Life Technologies (Gaithersburg, Md.). The porcine transforming growth factor beta 1 (TGF-β) was purchased from PeproTech (Rocky Hill, N.J.). In all experiments cells at 40-50% confluency were serum starved for 24 h and treated with TGF-β (5 ng/ml) for 72 h. At the end conditioned media collected was centrifuged at 2000 g for 20 minutes and filtered through 0.2 μm filter to remove the intact cells and debris and stored at −80° C. until further processing. Cells in the culture dishes were lysed in RIPA buffer and processed for western immunoblotting for assessing the expression of epithelial and mesenchymal markers. Protein concentrations were determined using the BCA protein assay reagent from Pierce (Rockford, Ill., USA).

Sample preparation, SDS-PAGE and in-gel digestion: 7 ml of conditioned media from control and TGF-β treated cells from two independent biological replicates was buffer exchanged into 25 mM ammonium bicarbonate and the volume reduced to 100 μl using a 10 kDa MWCO filter (Millipore). Half of each replicate (approximately 20 μg protein from controls and 10 μg protein from TGF-β treatment) was solubilized in loading buffer and resolved using Novex 4-12% gradient gels (Invitrogen Life Technologies, Carlsbad, Calif.). Each lane was manually excised into 40 equal slices and each slice was transferred to a well of a 96-well plate. Proteins in each gel slice were robotically reduced with 10 mM dithiothreitol, alkylated with 50 mM iodoacetamide, and digested with 160 ng trypsin (ProGest, Genomic Solutions, Ann Arbor, Mich.). Tryptic peptides were analyzed following acidification with 0.5% formic acid to a final pH 3.8. The volume of peptide mixture for each band was 40 µl. (Bhattacharjee et al., Proc Natl Acad Sci USA 98:13790-5, 2001).

Data-dependent LC/MS/MS: 30 µl of each digested gel slice was analyzed using nanoLC/MS/MS on a LTQ Orbitrap XL tandem mass spectrometer (ThermoFisher, San Jose, Calif.). Sample was loaded onto an IntegraFrit (New Objective, Woburn, Mass.) 75 µm×3 cm vented column packed with 0.5 mm Jupiter C12 material (Phenomenex, Torrance, Calif.) at 10 µl/min. Peptides were eluted with a 50 min gradient (0.1-30% B in 35 min, 30-50% B in 10 min and 50-80% B in 5 min where A=99.9% H2O, 0.1% acetonitrile in 0.1% formic acid and B=80% acetonitrile, 20% H2O in 0.1% formic acid) at 300 nL/min using a NanoAcquity HPLC pump (Waters, Beverley, Mass.) over a 75 µm×15 cm IntegraFrit analytical column packed also with Jupiter C12 material. The column was coupled to a 30 µm ID×3 cm stainless steel emitter (ThermoFisher, USA). MS was performed in the Orbitrap at 60,000 FWHM resolution, MS/MS was performed in the LTQ on the top six ions in each MS scan using the data-dependent acquisition mode. Normalized collision energy was set at 35% and 1 microscan was used with Automatic Gain Control (AGC) implementation. AGC enables the trap to fill with ions to the set ion target values. Target values for MS and MS/MS were $5 \times 10^4$ and $1.5 \times 10^3$ counts, respectively. Dynamic exclusion and repeat settings ensured each ion was selected only once and excluded for 30 s thereafter.

Data Processing: Data were processed using the MaxQuant v1.0.13.8 software, which provides protein identifications at a target false discovery rate (FDR). This version of MaxQuant utilizes a locally stored copy of the Mascot search engine (version 2.2, Matrix Science, London, UK) and data was searched against the IPI Human v3.53 protein database. Search parameters were: product ion mass tolerance 0.5 Da, 2 missed cleavages allowed, fully tryptic peptides only, fixed modification of carbamidomethyl cysteine, variable modifications of oxidized methionine, N-terminal acetylation and pyro-glutamic acid on N-terminal glutamine. Selected MaxQuant parameters were: "singlets" mode, peptide, protein and site FDR 1%, min. peptide length of 5 amino acids, minimum of one unique peptide per protein. Proteins identified by this (Lacroix et al., Expert Rev Mol Diagn 8:167-78, 2008).

Analysis are summarized in Table 51. In MaxQuant the quantitative measure of each protein is based on the sum of the chromatographic peak area of each peptide matched, termed "intensity" For each protein a Log 2 ratio of expression is determined by comparing the average intensity for that protein between the replicates of TGF-β treated and controls. A protein is determined as differentially expressed if it has more than two fold change in either direction. Log 2 ratio>1 is considered as upregulation and <1 is considered as down regulation.

Annotation of secreted proteins and mapping to gene expression: Proteins were annotated as secreted using multiple different bioinformatic tools including SecretomeP (Bendtsen et al., Protein Eng Des Sel 17:349-56, 2004) for non-classical and leaderless secreted proteins, TMHMM, an HMM-based method for prediction of transmembrane domains (Moller et al., Bioinformatics 17:646-53, 2001), SignalP package that detects signal peptides and predicts classical secreted proteins (Bendtsen et al., J Mol Biol 340:783-95, 2004), PSORT II that predicts the protein sub-cellular localization (Nakai et al., Trends Biochem Sci 24:34-6, 1999), and Secreted Protein Database (SPD) (Chen et al., Nucleic Acids Res 33:D169-73, 2005). Others were annotated as secreted proteins based on reported empirical evidence and GO analysis.

Entrez gene identifiers corresponding to the IPI accession numbers of identified proteins were obtained using human IPI cross reference data ("IPI.genes.HUMAN" for IPI human release 3.65). Entrez gene identifiers were used to obtain the corresponding probe set identifiers for the associated arrays from the Affymetrix annotation. Following the above protocol all the annotated secreted proteins were mapped to previously published TGF-β-induced EMT time course gene expression data set (GSE 17708) from the same cell line at identical conditions (Sartor et al., Bioinformatics 26:456-63). To match the secretome, differentially expressed genes only at 72 h time point (5057 probes corresponding to 3397 genes) were used for mapping. Some probes that are identified as differentially-expressed but with no assigned gene symbol were excluded (Garber et al., Proc Natl Acad Sci USA 98:13784-9, 2001).

Gene set enrichment and hierarchical clustering analysis: ConceptGen is a concept and gene set enrichment analysis tool (Sartor et al., Bioinformatics 26:456-63) It will test a given list of genes for overlap and its significance with a specified concept or gene set which includes Gene Ontology (GO), direct protein interactions, transcriptional regulation, miRNA targets, gene expression datasets. Using this tool, we performed GO cellular component, cellular process and KEGG pathways enrichment analsysis for the 97-gene EASP. Statistically significant (p<0.001) concepts are presented as network graphs with nodes representing concepts or gene sets and edges representing statistical significance of enrichment.

For clustering, the lists of oncogenic pathways included in the analysis were compiled from the KEGG database, except for ESC list which was based on Porath et al., and Hassan et al., studies (Ben-Porath et al., Nat Genet 40:499-507, 2008; Hassan et al., Clin Cancer Res 15:6386-90, 2009). The expression value for each pathway, including EASP, is the arithmetic mean of all genes in that pathway giving a single value for each pathway in a given sample. Hierarchical clustering of the Shedden et al 442 lung adenocarcinoma tumors (Shedden et al., Nat Med 14:822-7, 2008) was performed for indicated oncogenic pathways along with EASP using TreeView, and correlations are presented as a heat map with columns representing individual tumors and rows representing the arithmetic mean of a pathway.

Primary tumor-derived gene expression data sets and patient characteristics: Four published Affymetrix microarray data sets representing 908 lung tumors were used in the EASP survival analysis. The CEL files of microarray data were normalized using Robust Multi-array Average (RMA) method (Irizarry et al., Biostatistics 4:249-64, 2003). Shedden et al., 442 lung adenocarcinomas (Shedden) were used as training set (Shedden et al., Nat Med 14:822-7, 2008). The other three data sets were used as test sets which included Bild et al., 111 adenocarcinomas and squamous cell carcinoma data set (Bild) (Bild et al., Nature 439:353-7, 2006), Okayama et al., 226 early stage (stages 1 and 2) adenocarcinoma data set (Okayama) (Okayama et al., Cancer Res 72:100-11, 2012), and Raponi's 129 squamous cell carcinoma data set (Raponi) (Raponi et al., Cancer Res 66:7466-72, 2006). The patient characteristics and clinical information for these four data sets are provided in Table 2. At the primary end point was 5 year survival (Buyse et al., J Natl Cancer Inst 98:1183-92, 2006).

Statistical analysis method: The random survival forests developed in R package by Ishwaran et al (Ishwaran H, U.B UBK: Random survival forests for R. R News 7:7, 2007; Ishwaran et al., Ann. Appl. Statist 2:20, 2008) was employed for the EASP survival analysis of the four microarray data sets of lung cancer, as described before (Chen et al., J Thorac Oncol 6:1481-7, 2011). Briefly, The Random Survival Forest (RSF) is an ensemble tree method for analysis of right-censored survival data. Each decision tree of forests was grown by splitting patients by comparing survival differences via log-rank test based on a randomly selected subset of variables at each node. The 1000 trees were grown for each RSF. Once trees were built, test sets were dropped down to the trees for prediction. The cumulative hazard function (CHF) was derived from each tree, and an ensemble CHF, an average over 1000 survival trees, was determined. Mortality was obtained as a weighted sum over ensemble CHF, weighted by the number of individuals at risk at the different time points. Higher mortality values imply the higher risk. Mortality was used as risk index to separate patients into three risk groups (high, medium and low-risk, one third each group) and present Kaplan-Meier survival curves for each group. Each tree provides a measure of its predictive error as described by Ishwaran et al., (supra) with smaller number indicating a better tree. The prediction error is calculated by 1−C-index (i.e. the Harrell's concordance index) in the out-of-bag data which were not used for building a tree each time.

Variable importance scores (VIMPs) for all the variables used to grow trees were also generated. Large VIMPs indicate variables as good predictors for outcome whereas zero or negative values identify non-predictive. These scores were used to refine the 97-gene EASP to the 20-gene rEASP.

Cox proportional hazards regression model, Kaplan-Meier survival curve and log-rank test were used for survival analysis of individual genes or mortality index derived from RSF. The t test was used to assess the difference of mean expression of EASP signature in clinical and pathological groups including stage, differentiation and nodal status.

Results

Quantitative identification of differentially secreted proteins during EMT: For the analysis of secreted proteins, A549 lung adenocarcinoma cells were cultured in the serum-free media, stimulated with TGF-β for 72 h to induce EMT, and the conditioned media were collected from control and TGF-β treated cells for the analysis of differentially secreted proteins. Induction of EMT was confirmed by assessing E-cadherin, N-cadherin and vimentin expression in the cells by western immunoblotting as described before (Keshamouni et al., J Proteome Res 8:35-47, 2009; Keshamouni et al., J Proteome Res 5:1143-54, 2006). Proteins in the conditioned media from two different biological replicates were fractionated by SDS-PAGE. Each lane on the gel was cut into 40 slices. Proteins in each gel slice were subjected to trypsin digestion and analysed by LC-MS/MS on a LTQ-Orbitrap mass spectrometer. The resulting MS/MS spectra were analysed for protein identification and quantitation using MAXQUANT as described under methods. A total of 2410 proteins were identified, of which 1647 (70%) proteins were annotated as secreted using the multiple data bases and strategies described in Methods. With the criteria of at least two-fold change, 136 proteins were identified as increased in secretion (log 2 ratio>1) and 94 proteins as decreased in secretion (log 2 ratio<-1) during EMT.

Among the differentially secreted proteins various categories of proteins were observed, including increased secretion of proteases (MMP2, MMP9, BMP1), ECM components (collagens, fibronectin, versican and SPARC), cytokines (CTGF) and cell surface receptors (mucins, CD59) that are consistent with the migratory, invasive and immune evasive abilities confered by EMT and their regulation by TGF-β.

EMT associated secretory phenotype (EASP): To identify a gene signature that is representative of EMT and serves as a reliable biomarker for patient prognosis, the differentially secreted protein profile was interrogated with the corresponding gene expression profile (Sartor et al., Bioinformatics 26:456-63), from the same cell line and under identical conditions. To match with the secretome, differentially expressed genes only at 72 h time point were used for integration from the time course data set. Since the goal is to derive a measurable signature, only proteins whose secretion is induced during EMT were considered. By integrating gene and protein expression, 97 genes were identified that are upregulated at mRNA level by at least two-fold (p>0.01) and increased in secretion at the protein level by at least two-fold irrespective of p-value and defined them as EASP (Table 1). Given the stringent p-value cut-off used for mRNA expression and minimum two-fold change used for concordance between mRNA and protein, the p-value was not used for protein expression in defining EASP.

For functional interpretation, EASP was subjected to gene set enrichment analysis using ConceptGen (Sartor et al., supra). Analysis for cellular components has associated EASP with extracellular matrix, proteinaceous extracellular, collagen, basement membrane, matrix space, matrix part and matrix region part (FIG. 1A), consistent with their annotation as secretory proteins. More importantly enrichment analysis for biological processes has associated EASP with the cellular processes including cell adhesion, motility, actin cytoskeleton reorganization, coagulation, acute inflammatory response, proteolysis and response to wounding and external stimuli (FIG. 1A). Moreover, this also demonstrates that EASP is a true representation of EMT and serves as a reliable biomarker to track EMT.

Figure 1B:
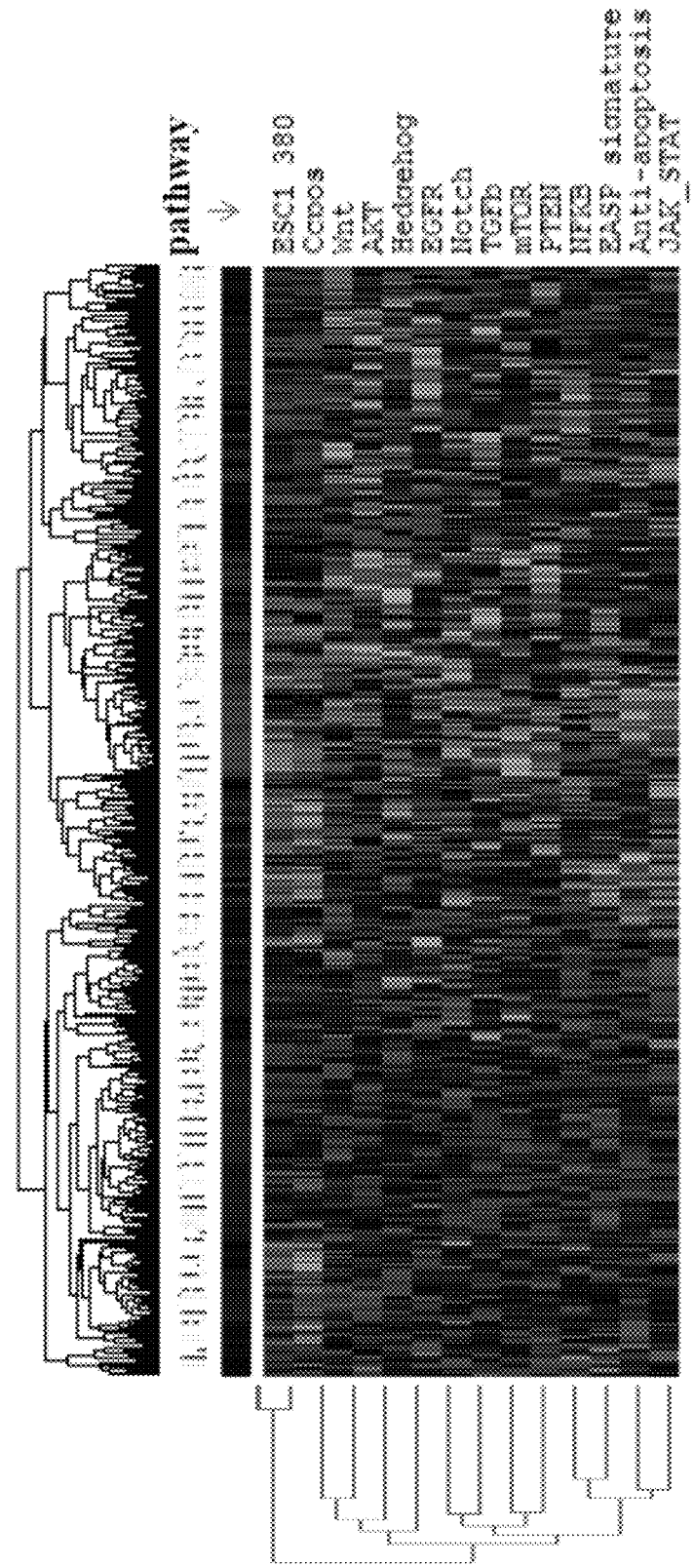

To assess the correlation of EASP with other known oncogenic pathways, hierarchical clustering of 442 lung adenocarcinomas based on their mean gene expression of the indicated pathway was performed. Clustering analysis yielded two distinct lung adenocarcinoma tumor groups with 50% tumors demonstrating higher expression of all pathways. Mean EASP expression pattern correlated with mean gene expression of all the oncogenic pathways tested. These include NF-kβ, anti-apoptosis, JAK-STAT, Notch, AKT, WNT pathways and embryonic stem cells (ESC) signature (FIG. 1B). All these pathways are known to be deregulated in lung adenocarcinomas and were implicated in the regulation of EMT.

Figure 2A:
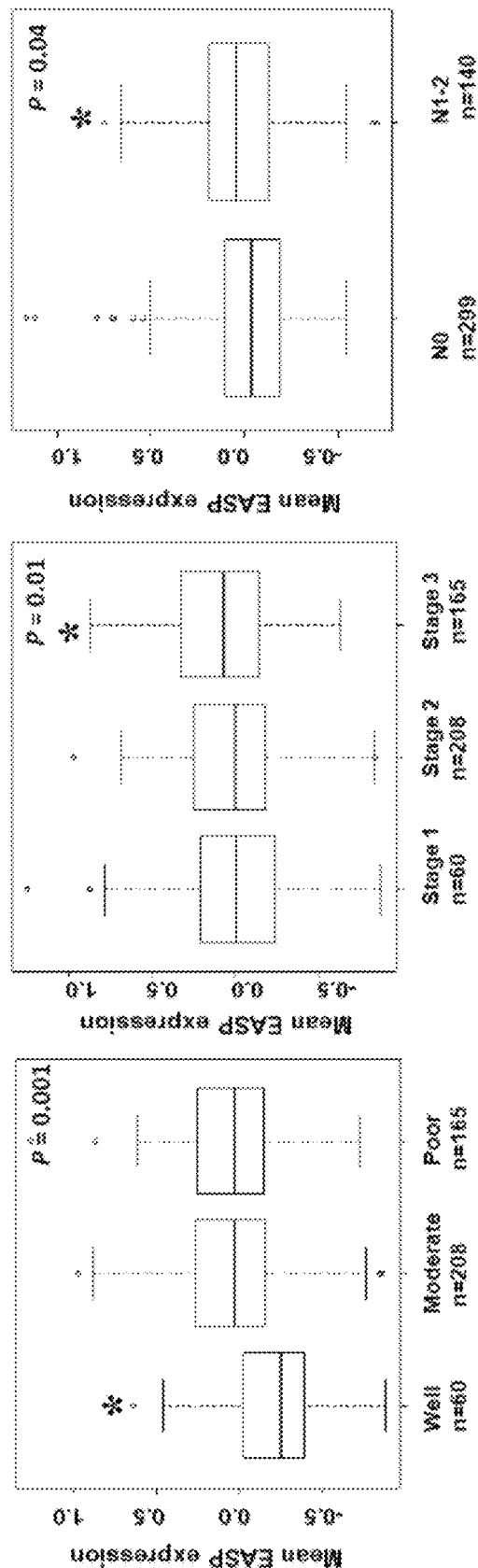
FIG. 2A-B shows (A) boxplot of EASP signature expression with differentiation, stage and lymph nodal status. (B) testing of 97-gene EASP prognosis signature as a predictor of lung cancer patient's survival.

Correlation of EASP with clinical variables: The ability of the EASP signature to stratify the patients based on tumor stage, differentiation and nodal status using the gene expression data derived from the Shedden et al 442 lung adenocarcinoma patients was determined (Shedden et al., Nat Med 14:822-7, 2008) (FIG. 2A). The EASP signature was able to identify the patients with well differentiated tumors from moderately and poorly differentiated tumors (P<0.001). Similarly the EASP signature was able to separate patients with stage I tumors from stage II and stage III tumors (P=<0.01). Furthermore the EASP signature expression is high in patients with positive nodal status (N1-2) compared to patients with negative nodal status (N0). Together these results indicate the clinical utility of EASP in predicting aggressive tumor behavior.

Figure 2B:
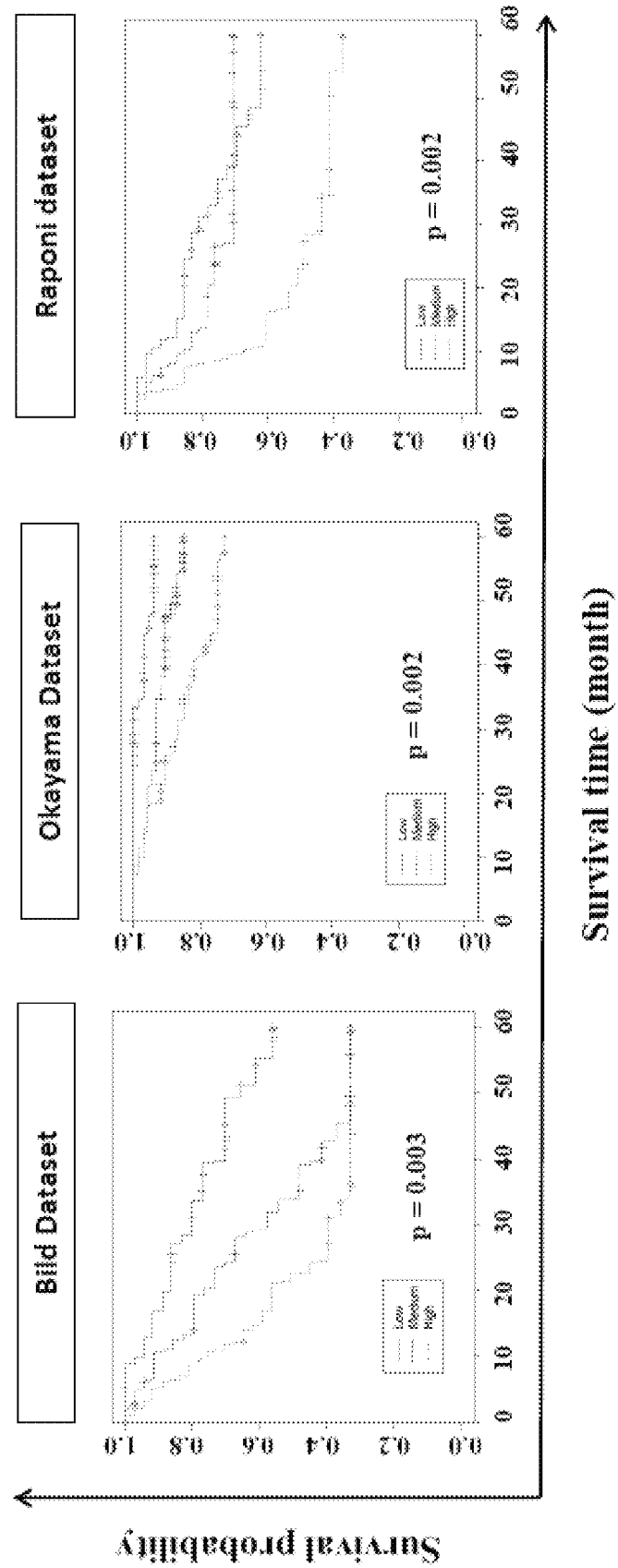

EASP stratifies lung cancer patients into low, medium and high-risk groups with distinct survival: In order to investigate whether the 97-gene EASP signature could predict the overall survival in NSCLC patients, the Shedden data set (n=442) was used as training set, As detailed in Methods, a mathematical model based on an RSF algorithm was built in the training set to predict the prognostic significance of EASP with stage, age and sex included. After locking down the model, it was tested in three independent publicly available lung cancer data sets, Bild et al, (n=111) (Nature 439:353-7, 2006), Okayama et al, (n=226) (Cancer Res 72:100-11, 2012) and Raponi et al, (n=129) (Cancer Res 66:7466-72, 2006). These cohorts include lung adenocarcinoma and squamous cell carcinoma patients. The prediction error rates were 33.6%, 30.0% and 36.7%, respectively for the Bild, Okayama and Raponi data sets (Table 4). The usefulness of RSF predictors was tested using a univariate Cox model with the mortality index as a continuous measure. The RSF prediction was significant for the Bild test set (likelihood ratio test (LRT P=0.00008), Okayama test set (LRT P=0.005) and Raponi test set (LRT P=0.02). In all three test sets low, medium and high-risk groups were clearly separated by mortality index (FIG. 2B). The Hazard Ratios were 1.00, 2.17 and 3.16 for the Bild data set (logrank test, P=0.003); 1.00, 2.60 and 5.37 for Okayama data set (logrank test, P=0.002); and 1.00, 0.96 and 2.61 for the Raponi data set (logrank test, P=0.002), respectively, for low, medium and high-risk groups (Table 4).

Figure 3:
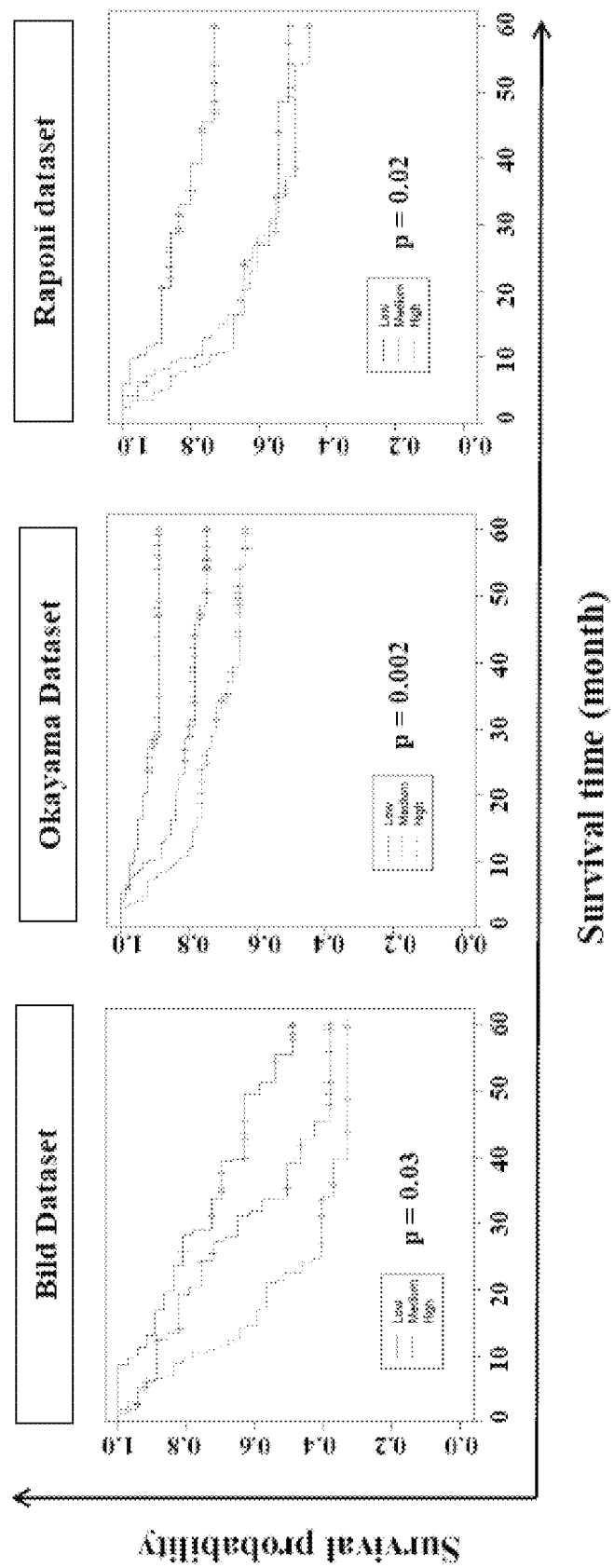
FIG. 3 shows testing of 20-gene rEASP prognosis signature as a predictor of lung cancer patient's survival.
Figure 4:
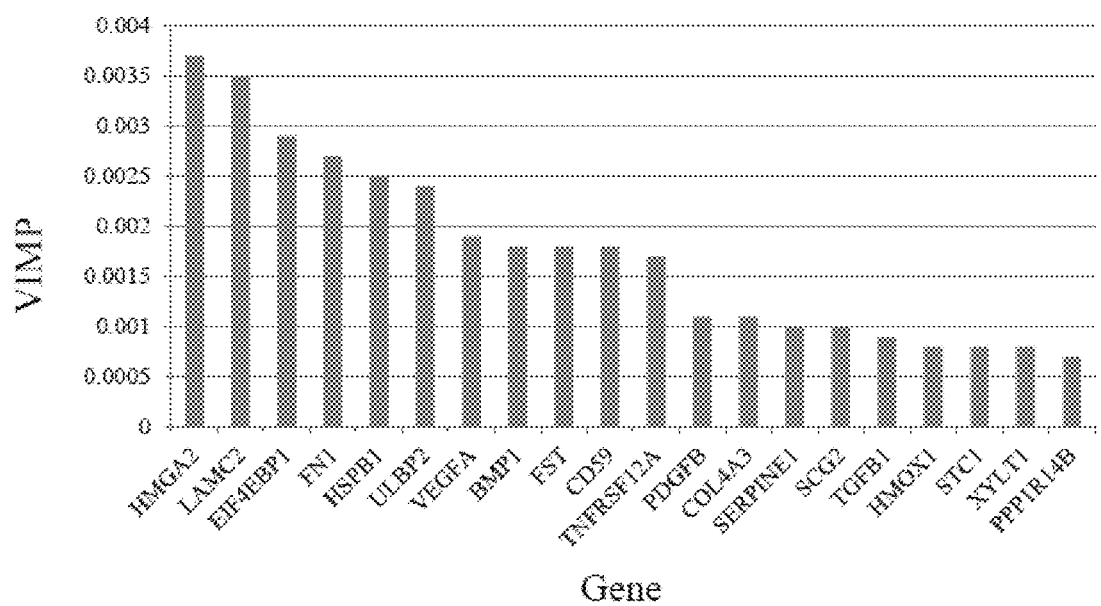
FIG. 4 shows variable importance scores (VIMP) of top 20 genes used in Random survival forest (RSF) in Shedden 442 training set.

Refining the 97-gene EASP to the 20-gene rEASP: In order to refine the EASP into a smaller gene subset that remains as effective in predicting survival of lung cancer patients, the 97-gene EASP was filtered based on the variable importance (VIMP) scores generated by RSF analysis of the Shedden et al, 442 data set. Higher VIMP values indicate variables with predictive ability whereas zero or negative values identify non-predictive variables. This resulted in a refined EASP (rEASP) comprising the top 20 genes with higher VIMP scores (FIG. 4). To assess whether the 20-gene rEASP performs as well as the 97-gene EASP signature in predicting patient survival, another model based on RSF algorithm was built to predict the prognostic significance of rEASP with stage, age and sex included, using Shedden data set (n=442) as training set. Next, the predictive power of this 20-gene rEASP model was tested in all three independent test sets described above (Bild, Raponi and Okayama) with clinical information in Table-2. The prediction error rates were 35.6%, 29.9% and 36.4%, respectively for the Bild, Okayama and Raponi data sets (Table 3). The usefulness of RSF predictors was tested using a univariate Cox model with the mortality index as a continuous measure. The RSF prediction was significant for the Bild test set (likelihood ratio test (LRT P=0.002), Okayama test set (LRT P=0.0004) and Raponi test set (LRT P=0.007). In all three test sets low, medium and high-risk groups were clearly separated by mortality index (FIG. 3). The Hazard Ratios were 1.00, 1.54 and 2.34 for the Bild data set (logrank test, P=0.03); 1.00, 2.37 and 3.75 for Okayama data set (logrank test, P=0.002); and 1.00, 2.38 and 2.79 for the Raponi data set (logrank test, P=0.02), respectively, for low, medium and high-risk groups (Table 3).

Contrary to the perception that tumor metastasis progresses in a linear and step-wise fashion, recent evidence suggests that a subset of tumors harbor molecular alterations at an early stage that are indicative of bad prognosis and poor patient survival (Ramaswamy et al., Nat Genet 33:49-54, 2003). This demonstrates the importance of identifying molecular changes at an early stage that dictate clinical behavior. The current system of TNM staging cannot identify such changes. There is an urgent need to develop prognostic tests that can predict recurrence and identify high-risk patients at an early stage when they would benefit from adjuvant therapy (Felip et al., Ann Oncol 16 Suppl 1:i28-9, 2005; Scagliotti et al., J Natl Cancer Inst 95:1453-61, 2003; Johnson et al., Clin Cancer Res 11:5022s-5026s, 2005; Keller et al., N Engl J Med 343:1217-22, 2000; Domont et al., Semin Oncol 32:279-83, 2005). Demonstrating the utility of such a prognostic test, a 70-gene signature (Buyse et al., J Natl Cancer Inst 98:1183-92, 2006) (Mammaprint, Agendia, The Netherlands) has been approved by FDA for breast cancer patients (Evolution of Translational Omics: Lessons Learned and the Path Forward, The National Academies Press, 2012). A 21-gene signature (Paik, Oncologist 12:631-5, 2007) (Oncotype DX, Genome Health, CA) is approved for breast cancers, with analogous signatures under development for prostate and colon cancers. Even though multiple gene, protein, auto-antibodies and miRNA-based profiles have been proposed for lung cancer prognosis, none to date has been approved for clinical use.

The predominant approach in deriving most of the prognostic signatures has been, profiling differentially occurring molecular changes between good versus bad outcome groups, without any consideration to the underlying tumor biology. Here a new approach to identify predictive biomarkers by profiling the complex cellular process of EMT, which is implicated in the initiation of tumor metastasis is described. The rationale behind this approach is that identifying proteins secreted during the course of a critical biological process that promotes a metastatic phenotype would provide relevant, reliable and robust prognostic biomarkers. In addition, one can measure EASP at the mRNA level and also at the protein level, because the biomarkers of EASP are based on the strong concordant expression of both mRNA and protein. Given that EMT is the initiating event for metastasis and may result in the dissemination of tumor cells, measuring EASP in the primary tumor, tumor cells in bone marrow compartment and circulating tumor cells allows the ability to track disease progression.

Consistent with the functional attributes confered by EMT and its regulation by TGF-β, proteins were identified that are implicated in tumor cell adhesion, migration, invasion, immune evasive mechanisms, extracellular matrix components, and tumor-stromal interactions. Gene set enrichment analysis of the 97-gene EASP, which is the subset of all up regulated proteins and their mRNAs, also identified biological processes that are reflective of EMT and TGF-β biology. Similarly, even the proteins in rEASP are representative of the functional EMT phenotype. Furthermore, clustering analysis of EASP with key oncogenic pathways showed a similar correlation to the expression of various pathways that are deregulated in lung adenocarcinomas. These include NF-kβ, anti-apoptosis, JAK-STAT, PTEN, AKT, WNT, Notch, Hedgehog and EGFR signaling pathways (Faivre et al., Semin Oncol 33:407-20, 2006; Sun et al., J Clin Invest 117:2740-50, 2007). Most importantly, the correlation of EASP expression with embryonic stem cell (ESC) signature is consistent with the recent finding that the ESC signature is associated with poor prognosis and worse overall survival in lung adenocarcinoma patients (Hassan et al., Clin Cancer Res 15:6386-90, 2009). This correlation is also consistent with finding that EMT may confer stem cell like properties to breast cancer cells (Mani et al., Cell 133:704-15, 2008). Together, these observations demonstrate that EASP not only reflects the heterogeneity and complexity associated with oncogenesis of lung cancer, but also demonstrates the significance and relevance of EASP biomarkers to the underlying biology of tumor metastasis.

Consistent with its prognostic significance EASP distinguished well from moderate or poorly-differentiated tumors and stage 1 from stage 2 and 3 patients. Most importantly it was strongly correlated with positive lymph node status, which is an important prognostic factor that influences the therapeutic decision making and probability of lung cancer recurrence. To test the clinical utility of EASP, the RSF analysis based survival model was built and trained on 442 primary lung adenocarcinoma tumor-derived gene expression data set, the largest lung cancer gene expression data set available with pathological, clinical and treatment annotations (Shedden et al., Nat Med 14:822-7, 2008). Using the variable importance (VIMP) scores from the training set (Shedden et al, supra), the EASP was refined into a subset of 20 genes (rEASP) with highest VIMP scores and tested its prognostic significance in three independent lung cancer data sets. Since the EASP was derived from an adenocarcinoma cell line, it was investigated whether EASP is specific to adenocarcinomas or does it have any relevance to other subtypes of lung cancer. To address this, the Okayama et al, data set of only adenocarcinomas (n=226), the Bild et al, data set of adenocarcinomas (n=58) and squamous cell carcinomas (n=53), and the Raponi et al, data set of only squamous cell carcinomas (n=129) were selected for independent testing. In all three independent test sets both EASP and rEASP based models were able to stratify patients into low, medium and high-risk groups with clearly separated mortality indexes and distinct hazard ratios. This demonstrates the relevance of these models for lung SCC. Since rEASP predicted the survival of early stage patients it, provides a prognostic signature to identify the high-risk early stage patients who might benefit the most from adjuvant therapy. Multiple inhibitors of EMT in lung cancer have been identified (Reka et al., Mol Cancer Ther 9:3221-32, 2010; Reka et al., J Thorac Oncol 6:1784-92, 2011). Such inhibitors find use in patients with high EASP expression.

TABLE 1

List of Genes that Constitute EASP with Corresponding Fold Change for Gene and Protein Expression. 20 Genes that are part of rEASP are in bold and underlined.

| Gene Symbol | Entrez ID | Protein Acc Id | Gene Title | Fold change (TGFβ/control) | |
|---|---|---|---|---|---|
| | | | | Microarray | Secretome |
| ADAM19 | 8728 | IPI00011901 | a disintegrin and metalloproteinase domain 19 (meltrin beta) | 17.47 | 26.78 |
| ANGPTL4 | 51129 | IPI00153060 | angiopoietin-like 4 | 19.67 | 2.33 |
| AP1S2 | 8905 | IPI00909244 | Adaptor-related protein complex 1, sigma 2 subunit | 2.15 | 3.23 |
| ARPC4 | 10093 | IPI00925052 | actin related protein 2/3 complex, subunit 4, 20 kDa | 2.03 | 1.41 |
| BMP1 | 649 | IPI00014021 | bone morphogenetic protein 1 | 4.68 | 17.90 |
| BPGM | 669 | IPI00215979 | 2,3-bisphosphoglycerate mutase | 3.85 | 4.23 |
| CD151 | 977 | IPI00298851 | CD151 antigen | 1.81 | 2.09 |
| CD59 | 966 | IPI00011302 | CD59 antigen | 3.99 | 2.53 |
| CHST11 | 50515 | IPI00099831 | Carbohydrate (chondroitin 4) sulfotransferase 11 | 4.62 | 4.00 |
| CHST3 | 9469 | IPI00306853 | carbohydrate (chondroitin 6) sulfotransferase 3 | 4.30 | 3.61 |
| COL1A1 | 1277 | IPI00297646 | collagen, type I, alpha 1 | 10.11 | 3.44 |
| COL4A1 | 1282 | IPI00743696 | collagen, type IV, alpha 1 | 62.47 | 5.41 |
| COL4A2 | 1284 | IPI00306322 | collagen, type IV, alpha 2 | 15.99 | 5.24 |
| COL4A3 | 1285 | IPI00010360 | collagen, type IV, alpha 3 (Goodpasture antigen) | 3.18 | 4.57 |
| COL7A1 | 1294 | IPI00025418 | collagen, type VII, alpha 1 | 3.42 | 1.35 |
| CRIP2 | 1397 | IPI00921911 | cysteine-rich protein 2 | 2.86 | 19.22 |
| VCAN | 1462 | IPI00215628 | chondroitin sulfate proteoglycan 2 (versican) | 2.97 | 1.89 |
| CTGF | 1490 | IPI00020977 | connective tissue growth factor | 4.96 | 4.37 |
| CXCL12 | 6387 | IPI00719836 | chemokine (C—X—C motif) ligand 12 (stromal cell-derived factor 1) | 5.56 | 17.71 |
| CYR61 | 3491 | IPI00299219 | cysteine-rich, angiogenic inducer, 61 | 5.66 | 2.16 |
| DSC2 | 1824 | IPI00025846 | desmocollin 2 | 4.12 | 3.15 |
| ECM1 | 1893 | IPI00645849 | extracellular matrix protein 1 | 2.09 | 3.64 |
| EFNA1 | 1942 | IPI00025840 | ephrin-A1 | 1.72 | 1.14 |
| EIF4EBP1 | 1978 | IPI00002569 | eukaryotic translation initiation factor 4E binding protein 1 | 1.94 | 20.54 |
| EPHB2 | 2048 | IPI00021275 | EPR receptor B2 | 8.07 | 1.76 |
| FHL2 | 2274 | IPI00396967 | four and a half LIM domains 2 | 3.15 | 3.31 |
| FN1 | 2335 | IPI00845263 | Fibronectin 1 | 5.14 | 3.15 |
| FST | 10468 | IPI00021081 | follistatin | 6.45 | 1.30 |
| FSTL1 | 11167 | IPI00029723 | follistatin-like 1 | 5.14 | 2.18 |
| FSTL3 | 10272 | IPI00025155 | follistatin-like 3 (secreted glycoprotein) | 3.98 | 2.21 |
| C11orf41 | 25758 | IPI00852979 | G2 protein | 3.98 | 20.18 |
| GALNT2 | 2590 | IPI00004669 | UDP-N-acetyl-alpha-D-galactosamine:polypeptide N-acetylgalactosaminyltransferase 2 (GalNAc-T2) | 2.78 | 1.69 |
| GSN | 2934 | IPI00646773 | gelsolin (amyloidosis, Finnish type) | 3.99 | 2.70 |
| HMGA2 | 8091 | IPI00005996 | high mobility group AT-hook 2 /// high mobility group AT-hook 2 | 4.20 | 3.13 |
| HMOX1 | 3162 | IPI00215893 | heme oxygenase (decycling) 1 | 3.41 | 17.36 |
| HSPB1 | 3315 | IPI00025512 | heat shock 27 kDa protein 1 | 2.28 | 2.42 |
| IGF1 | 3479 | IPI00433029 | insulin-like growth factor 1 (somatomedin C) | 4.65 | 1.11 |
| IGF2 | 3481 | IPI00215977 | insulin-like growth factor 2 (somatomedin A) | 1.03 | 1.87 |

TABLE 1-continued

List of Genes that Constitute EASP with Corresponding Fold Change for Gene and
Protein Expression. 20 Genes that are part of rEASP are in bold and underlined.

| Gene Symbol | Entrez ID | Protein Acc Id | Gene Title | Fold change (TGFβ/control) Microarray | Fold change (TGFβ/control) Secretome |
|---|---|---|---|---|---|
| IGFBP5 | 3488 | IPI00029236 | insulin-like growth factor binding protein 5 | 21.60 | 7.17 |
| IGFBP7 | 3490 | IPI00016915 | insulin-like growth factor binding protein 7 | 63.94 | 5.33 |
| IL11 | 3589 | IPI00025820 | interleukin 11 | 39.43 | 5.57 |
| INHBA | 3624 | IPI00028670 | Inhibin, beta A (activin A, activin AB alpha polypeptide) | 24.32 | 25.47 |
| ITGA2 | 3673 | IPI00013744 | Integrin, alpha 2 (CD49B, alpha 2 subunit of VLA-2 receptor) | 5.13 | 1.15 |
| ITGA3 | 3675 | IPI00290043 | Integrin, alpha 3 (antigen CD49C, alpha 3 subunit of VLA-3 receptor) | 1.90 | 1.80 |
| JAG1 | 182 | IPI00099650 | Jagged 1 (Alagille syndrome) | 3.10 | 1.87 |
| MGC17330 | 113791 | IPI00298388 | phosphoinositide-3-kinase interacting protein 1 | 2.53 | 20.35 |
| KIAA1797 | 54914 | IPI00748360 | KIAA1797 | 1.70 | 19.36 |
| LAMC2 | 3918 | IPI00015117 | laminin, gamma 2 | 20.02 | 7.45 |
| LEFTY2 | 7044 | IPI00010893 | left-right determination factor 2 | 2.23 | 23.89 |
| LIF | 3976 | IPI00009720 | leukemia inhibitory factor (cholinergic differentiation factor) | 2.71 | 2.22 |
| XYLT1 | 64131 | IPI00183487 | hypothetical protein LOC283824 | 12.13 | 23.61 |
| LTBP1 | 4052 | IPI00784258 | latent transforming growth factor beta binding protein 1 | 2.86 | 2.25 |
| LTBP2 | 4053 | IPI00292150 | latent transforming growth factor beta binding protein 2 | 9.42 | 4.66 |
| LTBP3 | 4054 | IPI00073196 | latent transforming growth factor beta binding protein 3 | 3.87 | 1.55 |
| LTBP4 | 8425 | IPI00873371 | latent transforming growth factor beta binding protein 4 | 3.01 | 2.14 |
| PIK3IP1 | 113791 | IPI00296388 | HGFL gene /// HGFL gene | 2.53 | 20.35 |
| MMP1 | 4312 | IPI00008561 | matrix metalloproteinase 1 (interstitial-collagenase) | 5.81 | 6.27 |
| MMP10 | 4319 | IPI00013405 | matrix metalloproteinase 10 | 20.03 | 25.23 |
| MMP2 | 4313 | IPI00027780 | matrix metalloproteinase 2 | 10.86 | 8.36 |
| MMP9 | 4318 | IPI00027509 | matrix metalloproteinase 9 | 1.34 | 22.00 |
| MRC2 | 9902 | IPI00005707 | mannose receptor, C type 2 | 4.97 | 1.47 |
| NPC2 | 10577 | IPI00301579 | Niemann-Pick disease, type C2 | 2.88 | 3.33 |
| NPTX1 | 4884 | IPI00220562 | neuronal pentraxin 1 | 7.29 | 7.41 |
| NRG1 | 3084 | IPI00221375 | neuregulin 1 | 3.27 | 2.19 |
| PAWR | 5074 | IPI00001871 | PRKC, apoptosis, WT1, regulator | 2.34 | 20.17 |
| PCDH1 | 5097 | IPI00672579 | protocadherin 1 (cadherin-like 1) | 4.48 | 22.09 |
| PDGFB | 5155 | IPI00000044 | platelet-derived growth factor beta polypeptide | 4.86 | 18.85 |
| PDLIM2 | 64236 | IPI00007983 | PDZ and LIM domain 2 (mystique) | 2.74 | 16.79 |
| PGRMC2 | 10424 | IPI00005202 | progesterone receptor membrane component 2 | 1.85 | 2.20 |
| PLAT | 5327 | IPI00019590 | plasminogen activator, tissue | 4.41 | 19.85 |
| PLAUR | 5329 | IPI00010676 | plasminogen activator, urokinase receptor | 3.07 | 2.22 |
| PLOD2 | 5352 | IPI00337495 | procollagen-lysine, 2-oxoglutarate 5-dioxygenase 2 | 2.81 | 2.03 |
| PLSCR3 | 57048 | IPI00216127 | phospholipid scramblase 3 | 2.25 | 3.22 |
| PPP1R14B | 26472 | IPI00398922 | protein phosphatase 1, regulatory (inhibitor) subunit 14B | 2.11 | 1.55 |
| HTRA1 | 5654 | IPI00003176 | protease, serine, 11 (IGF binding) | 2.63 | 3.00 |
| PTPRK | 5796 | IPI00470937 | protein tyrosine phosphatase, receptor type, K | 6.19 | 1.64 |
| RSU1 | 6251 | IPI00847168 | Ras suppressor protein 1 | 2.00 | 1.41 |
| SCG2 | 7857 | IPI00009362 | secretogranin II (chromogranin C) | 31.96 | 7.63 |
| SEMA3C | 10512 | IPI00019209 | sema domain, immunoglobulin domain (Ig), short basic domain, secreted, (semaphorin) 3C | 4.87 | 3.70 |
| SERPINE1 | 5054 | IPI00007118 | serine (or cysteine) proteinase inhibitor, clade E (nexin, plasminogen activator inhibitor type 1), member 1 | 41.73 | 4.13 |
| SERPINE2 | 5270 | IPI00009890 | Serine (or cysteine) proteinase inhibitor, clade E (nexin, plasminogen activator inhibitor type 1), member 2 | 17.90 | 4.36 |
| SPOCK1 | 6695 | IPI00005292 | sparc/osteonectin, cwcv and kazal-like domains proteoglycan (testican) | 70.53 | 5.84 |
| STC1 | 6781 | IPI00005564 | Stanniocalcin 1 | 10.09 | 3.99 |
| TAGLN | 6876 | IPI00216138 | transgelin | 13.35 | 6.44 |
| TAGLN2 | 8407 | IPI00647915 | transgelin 2 | 2.24 | 1.17 |
| TAX1BP3 | 30851 | IPI00005585 | Tax1 (human T-cell leukemia virus type I) binding protein 3 | 1.83 | 3.54 |
| TGFB1 | 7040 | IPI00000075 | transforming growth factor, beta 1 | 2.57 | 2.22 |
| TGFBR1 | 7046 | IPI00005733 | Transforming growth factor, beta receptor 1 | 5.72 | 2.72 |
| THBS1 | 7057 | IPI00296099 | thrombospondin 1 | 16.73 | 4.71 |
| TIMP2 | 7077 | IPI00027166 | tissue inhibitor of metalloproteinase 2 | 4.72 | 2.54 |
| TLL2 | 7093 | IPI00465231 | tolloid-like 2 | 2.59 | 2.15 |
| TNFAIP6 | 7130 | IPI00303341 | tumor necrosis factor, alpha-induced protein 6 | 5.03 | 7.48 |
| TNFRSF12A | 51330 | IPI00010277 | tumor necrosis factor receptor superfamily, member 12A | 5.10 | 1.83 |
| TP53I3 | 9540 | IPI00384643 | tumor protein p53 inducible protein 3 | 3.35 | 2.47 |
| TUBA4B | 80086 | IPI00017454 | tubulin, alpha 4 | 2.24 | 2.20 |
| ULBP2 | 80328 | IPI00018660 | UL16 binding protein 2 | 5.18 | 3.51 |
| VEGFA | 7422 | IPI00012567 | vascular endothelial growth factor | 4.66 | 2.86 |

TABLE 2

Clinical Characteristics of Sample Used in This Study

| Data set | Shedden set | Bild set | Raponi set | Okayama set |
|---|---|---|---|---|
| Sample number | 442 | 111 | 129 | 226 |
| Type of cancer | Ad | 58 Ad/53 SCC | SCC | Ad |
| Age average | 64.4 | 64.8 | 67.5 | 59.6 |
| Gender | | | | |
| Female | 219 | 48 | 48 | 121 |
| Male | 224 | 63 | 82 | 105 |
| Stage | | | | |
| Stage I | 276 | 67 | 73 | 168 |
| Stage II | 105 | 18 | 34 | 58 |
| Stage III | 59 | 21 | 23 | 0 |
| Differentiation | | | | |
| Well | 60 | NA | 15 | NA |
| Moderate | 209 | NA | 76 | NA |
| Poor | 167 | NA | 39 | NA |
| Dead (5 year) | 188 | 58 | 52 | 32 |
| Alive | 255 | 53 | 78 | 194 |
| Adjuvant therapy | | | | |
| Yes | 109 | | 48 | |
| No | 330 | | 69 | 204 |
| Unknown | 3 | 111 | 12 | 22 |

Abbreviation:
Ad, adenocarcinomas;
SCC, squamous cell cancer.
Adjuvant therapy includes chemo- and/or radio-therapy.

TABLE 3

Prediction Results of 20-gene rEASP Signature on Three Test Sets.

| | RSF* | Cox model** | Log rank test*** | | |
|---|---|---|---|---|---|
| | Test error rate | P | HR | 95% CI | P |
| Okayama test set (n = 226) | | | | | |
| | 29.9% | 0.0004 | | | |
| Low risk | | | 1 | | 0.002 |
| Medium risk | | | 2.37 | 1.03-5.46 | |
| High risk | | | 3.75 | 1.70-8.28 | |
| Raponi test set (n = 129) | | | | | |
| | 36.4% | 0.007 | | | |
| Low risk | | | 1 | | 0.02 |
| Medium risk | | | 2.38 | 1.12-5.10 | |
| High risk | | | 2.79 | 1.32-5.90 | |
| Bild test set (n = 111) | | | | | |
| | 35.6% | 0.002 | | | |
| Low risk | | | 1 | | 0.03 |
| Medium risk | | | 1.54 | 0.78-3.02 | |
| High risk | | | 2.34 | 1.24-4.42 | |

MRI = mortality risk index;
Med = Medium.
*RSF prediction model built from the 442 training set including 20 genes, age, gender and stage.
**MRI as continuous value, liklihood ratio test (LRT) was used in univariate Cox model.
***MRI separated test patients to 3 risk groups (low, medium and high risk, ⅓rd in each group).

TABLE 4

| | RSF* | Cox model** | Log rank test*** | | |
|---|---|---|---|---|---|
| | Test error rate | P | HR | 95% CI | P |
| Bild test set (n = 111) | | | | | |
| | 33.6% | 0.00008 | | | |
| Low risk | | | 1 | | 0.003 |
| Medium risk | | | 2.17 | 1.08-4.34 | |
| High risk | | | 3.16 | 1.60-6.24 | |
| Okayama test set (n = 226) | | | | | |
| | 30.0% | 0.005 | | | |
| Low risk | | | 1 | | 0.002 |
| Medium risk | | | 2.60 | 0.81-8.28 | |
| High risk | | | 5.37 | 1.82-15.88 | |
| Raponi test set (n = 129) | | | | | |
| | 36.7% | 0.02 | | | |
| Low risk | | | 1 | | 0.002 |
| Medium risk | | | 0.96 | 0.44-2.07 | |
| High risk | | | 2.61 | 1.36-5.01 | |

MRI = mortality risk index;
Med = Medium.
*RSF prediction model built from the 442 training set including 97 genes, age, gender and stage.
**MRI as continuous value, liklihood ratio test (LRT) was used in univariate Cox model.
***MRI separated test patients to 3 risk groups (low, medium and high-risk, ⅓rd in each group).

Although a variety of embodiments have been described in connection with the present disclosure, it should be understood that the claimed invention should not be unduly limited to such specific embodiments. Indeed, various modifications and variations of the described compositions and methods of the invention will be apparent to those of ordinary skill in the art and are intended to be within the scope of the following claims.

We claim:

1. A method for determining a gene expression profile of HMGA2, LAMC2, EIF4EBP1, FN1, HSPB1, ULBP2, VEGFA, BMP1, FST, CD59, TNFRSF12A, PDGFB, COL4A3, SERPINE1, SCG2, TGFB1, HMOX1, STC1, XYLT1, and PPP1R14B, comprising: a) performing a gene expression assay on a sample from a subject diagnosed with lung cancer to detect the level of gene expression of a set of genes consisting of HMGA2, LAMC2, EIF4EBP1, FN1, HSPB1, ULBP2, VEGFA, BMP1, FST, CD59, TNFRSF12A, PDGFB, COL4A3, SERPINE1, SCG2, TGFB1, HMOX1, STC1, XYLT1, and PPP1R14B using primers and/or probes to the specific genes.

2. The method of claim 1, wherein said lung cancer is lung adenocarcinoma or squamous cell carcinoma.

3. The method of claim 1, further comprising the step of determining a treatment course of action based on said gene expression profile.

4. The method of claim 1, wherein said primers and/or probes are 15 to 100 nucleotides in length and comprise a label selected from the group consisting of an enzymatic reporter molecule, a fluorescent reporter molecule, a radioactive reporter molecule, and a luminescent reporter molecule.

* * * * *